United States Patent
Pak et al.

(10) Patent No.: US 10,925,546 B2
(45) Date of Patent: Feb. 23, 2021

(54) SYSTEM AND METHOD FOR EVALUATING EFFECTS OF ANTIARRHYTHMIC AGENT

(71) Applicant: INDUSTRY-ACADEMIC COOPERATION FOUNDATION YONSEI UNIVERSITY, Seoul (KR)

(72) Inventors: Hui Nam Pak, Seoul (KR); Young Seon Lee, Seoul (KR)

(73) Assignee: INDUSTRY-ACADEMIC COOPERATION FOUNDATION YONSEI UNIVERSITY, Seoul (KR)

( * ) Notice: Subject to any disclaimer, the term of this patent is extended or adjusted under 35 U.S.C. 154(b) by 890 days.

(21) Appl. No.: 15/542,472

(22) PCT Filed: Jul. 28, 2015

(86) PCT No.: PCT/KR2015/007861
§ 371 (c)(1),
(2) Date: Jul. 10, 2017

(87) PCT Pub. No.: WO2016/111433
PCT Pub. Date: Jul. 14, 2016

(65) Prior Publication Data
US 2018/0271453 A1    Sep. 27, 2018

(30) Foreign Application Priority Data
Jan. 9, 2015  (KR) ................. 10-2015-0003617

(51) Int. Cl.
| | |
|---|---|
| *A61B 5/00* | (2006.01) |
| *A61B 5/0402* | (2006.01) |
| *A61B 5/042* | (2006.01) |
| *A61B 5/0205* | (2006.01) |
| *A61B 5/145* | (2006.01) |
| *G01N 33/15* | (2006.01) |
| *A61B 5/0245* | (2006.01) |

(52) U.S. Cl.
CPC .......... *A61B 5/7275* (2013.01); *A61B 5/0205* (2013.01); *A61B 5/0402* (2013.01); *A61B 5/042* (2013.01); *A61B 5/14546* (2013.01); *A61B 5/4848* (2013.01); *A61B 5/7235* (2013.01); *G01N 33/15* (2013.01); *A61B 5/0245* (2013.01)

(58) Field of Classification Search
CPC ... A61B 5/7275; A61B 5/0205; A61B 5/0402; A61B 5/042; A61B 5/4848; A61B 5/7235; G01N 33/15

USPC ............................................. 703/12
See application file for complete search history.

(56) References Cited

U.S. PATENT DOCUMENTS

| | | | |
|---|---|---|---|
| 2010/0179447 | A1 | 7/2010 | Hunt |
| 2016/0058520 | A1* | 3/2016 | Yang ............... G16H 50/50 703/11 |

FOREIGN PATENT DOCUMENTS

| | | |
|---|---|---|
| JP | 2008-86588 A | 4/2008 |
| JP | 2008-086588 A | 4/2008 |
| JP | 4565841 B2 | 10/2010 |
| JP | 4608217 B2 | 1/2011 |
| JP | 5161963 B2 | 3/2013 |
| KR | 10-1443156 B1 | 9/2014 |
| WO | 2012/151301 A1 | 11/2012 |

OTHER PUBLICATIONS

JPO Office Action, dated May 29, 2018, for Japanese Patent Application No. 2017-536567 which corresponds to the above-identified U.S. application.
SIPO Office Action, dated Dec. 14, 2018, for Chinese Patent Application No. 201580072890.X which corresponds to the above-identified U.S. application.
Search Report, dated Oct. 28, 2015, for International Application No. PCT/KR2015/007861.
Written Opinion, dated Oct. 28, 2015, for International Application No. PCT/KR2015/007861.

* cited by examiner

*Primary Examiner* — Jerry Lin
(74) *Attorney, Agent, or Firm* — LRK Patent Law Firm

(57) ABSTRACT

A system and method for evaluating effects of an antiarrhythmic agent. The system includes: an action potential measurement unit for measuring a cardiac action potential of a patient; an ion channel characteristics determination unit for determining ion channel characteristics of the patient using the cardiac action potential; and an antiarrhythmic agent effect evaluation unit for simulating a treatment effect of an antiarrhythmic agent by reflecting characteristics of the antiarrhythmic agent on the determined ion channel characteristics of the patient. The system can conveniently determine the patient's ion channel characteristics by measuring the cardiac action potential of the patient, thereby preventing the risk of gathering cardiomyocytes of the patient. In addition, the system can simulate a treatment effect of an antiarrhythmic agent that usually exhibits a different effect and a different level of safety depending on an individual's ion channel characteristics, without being directly applied to the patient.

17 Claims, 12 Drawing Sheets

SYSTEM AND METHOD FOR EVALUATING EFFECTS OF ANTIARRHYTHMIC AGENT

CROSS-REFERENCE TO RELATED APPLICATION(S)

The present application is a U.S. National Phase entry from International Application No. PCT/KR2015/007861, filed Jul. 28, 2015, which claims priority to Korean Patent Application No. 10-2015-0003617, filed Jan. 9, 2015, the disclosure of which is incorporated by reference herein in its entirety.

BACKGROUND OF THE INVENTION

1. Technical Field

The present invention relates to an antiarrhythmic agent effect evaluation system. More particularly, the present invention relates to an antiarrhythmic agent effect evaluation system capable of evaluating effects of an antiarrhythmic agent selected in accordance with a patient's ion channel characteristics.

2. Description of Related Art

Arrhythmia refers to a symptom in which the heartbeat is irregular, too fast, or too slow for a certain reason, for example, when an electrical impulse does not occur or cannot be transmitted in a heart. Such a condition may result in a stroke or sudden death.

Arrhythmia can be treated through surgery such as radiofrequency catheter ablation, which is a method of treating arrhythmia by terminating an electrical pathway in the heart through cauterization of heart tissue. This method has a problem that it is difficult to determine a proper invasion section to obtain an optimal effect before surgery. Therefore, antiarrhythmic agents have been recently popularly used for treatment of arrhythmia.

There are various kinds of antiarrhythmic agents which are classified into Classes I to IV. Each antiarrhythmic agent adjusts ion channels of heart cells. However, antiarrhythmic agents exhibit highly different effects and different levels of safety according to characteristics of ion channels of an individual. Therefore, if an individual's ion channel characteristics can be determined in advance, it is possible to selectively use a suitable antiarrhythmic agent that is most effective and can ensure safety for each patient. Moreover, it is possible to simulate a treatment effect based on the characteristics of the selected antiarrhythmic agent before administration to a patient.

The present invention provides a system and method for evaluating effects of an antiarrhythmic agent, the system and method being capable of determining an individual's ion channel characteristics and simulating a treatment effect of an antiarrhythmic agent suitably selected for the individual according to the individual's ion channel characteristics.

SUMMARY OF THE INVENTION

Accordingly, the present invention has been made keeping in mind the above problems occurring in the prior art, and an object of the present invention is to provide a system and method for evaluating effects of an antiarrhythmic agent, the system and method being capable of determining ion channel characteristics of a patient without gathering cardiomyocyte s of the patient.

Another object of the present invention is to provide a system and method for simulating effects of an antiarrhythmic agent, the system and method being capable of simulating a treatment effect of an antiarrhythmic agent that is determined and selected according to a patient's ion channel characteristics without applying the selected antiarrhythmic agent to the patient.

Technical problems to be solved by the present invention are not limited to the problems described above, but other various technical problems can be derived from the description described below, within a scope that is obvious to those who ordinarily skilled in the art, can be solved.

In order to accomplish the above object, according to one aspect, the present invention provides a system and method for evaluating effect s of an antiarrhythmic agent, the system including: a n action potential measurement unit that measures a cardiac action potential of a patient; an ion channel characteristics determination unit that determines a characteristic of an ion channel of the patient on the basis of the measured cardiac action potential; and an antiarrhythmic agent effect evaluation unit that simulates a treatment effect of an antiarrhythmic agent selected in accordance with the characteristic of the ion channel of the patient by reflecting a characteristic of the selected antiarrhythmic agent on the characteristic of the ion channel of the patient. According to this aspect, it is possible to simply determine a patient's ion channel characteristics by measuring a patient's cardiac action potential. Therefore, it is unnecessary to take a risk of gathering a patient's cardiomyocyte s, and it is possible to simulate a treatment effect of an antiarrhythmic agent suitably selected for the patient on the basis of the patient's ion channel characteristics without directly applying the selected antiarrhythmic agent to the patient.

In addition, the action potential measurement unit may measure a patient's cardiac action potential using a catheter and records the measured cardiac action potential using a pacing protocol, and may include: an ion channel value storage unit in which physiological conductance maximum values of all ion channels of an individual are stored; a parameter extraction unit that extracts physiological conductance maximum values of n ion channels associated with ion channel modeling from the physiological conductance value s stored in the ion channel value storage unit, sets the extracted values respectively as parameters P1 to Pn, and converts the parameters to have a uniform distribution; and a parameter set setting unit that randomly extracts a set of n parameters K or more times from the parameters P1 to Pn converted to have a uniform distribution and sets the K or more sets of the parameters respectively as parameter sets S1 to Sk.

In addition, the ion channel characteristics determination unit may include a parameter set selection unit that randomly selects one parameter set Si (i=K) from the parameter sets S1 to Sk M or more times; and a graph generation unit that simulatively executes a pacing protocol with respect to the selected M or more parameter sets Si and generates M or more graphs regarding a relationship between an action potential duration (APD) and a pacing interval. The ion channel characteristics determination may further include an ion channel characteristics deriving unit that extracts the physiological conductance values of the ion channels represented by n parameters included in a parameter set Sj extracted by the parameter set extraction unit from the ion channel value storage unit, thereby deriving a patient's ion channel characteristics.

The parameter set extraction unit may raise each difference between the action potential duration on each graph generated by the graph generation unit and the patient's cardiac action potential measured by the action potential measurement unit to the second power to produce squares of the respective differences, totals the squares, and calculate a square root of the sum of the squares to produce an error, in which n is 8, the n ion channels include INa, ICaL, IK1, IKr, INak, INaca, ITo, and IKur ion channels, and K and M are each 10,000.

According to another aspect, there is provided an antiarrhythmic agent effect evaluation method including: (a) measuring a cardiac action potential of a patient, using an action potential measurement unit; (b) determining ion channel characteristics of the patient, using an ion channel characteristics determination unit; (c) simulating a treatment effect of an antiarrhythmic agent by reflecting characteristics of the antiarrhythmic to the ion channel characteristics of the patient, using an antiarrhythmic agent effect simulative evaluation unit, in which in the step (b) includes: (b-1) extracting physiological conductance maximum values of n ion channels associated with ion channel modeling from among physiological conductance values stored in an ion channel value storage unit, setting the extracted values respectively as parameters P1 to Pn, and converting the parameters to have a uniform distribution, using a parameter extraction unit; (b-2) extracting a set of n parameters K or more times from the parameters P1 to Pn converted to have a uniform distribution and setting the K or more sets of the parameters respectively as parameter sets S1 to Sk, using a parameter set setting unit;
(b-3) randomly selecting one parameter set Si (i–K) from the parameter sets Si to Sk M or more times, using a parameter set selection unit; (b-4) performing simulative execution of a pacing protocol with respect to the selected parameter set Si (i=K) and generating M or more graphs regarding a relationship between an action potential duration (APD) and a pacing interval, using a graph generation unit; (b-5) calculating an error between an action potential duration on the graph generated by the graph generation unit and the cardiac action potential of the patient measured by the action potential measurement unit, and extracting a parameter set Sj (j=K) having an error range smaller than a predetermined value, using a parameter set extraction unit; and (b-6) deriving ion channel characteristics of the patient by extracting physiological conductance values of ion channels represented by the n parameters included in the parameter set Sj (j=K) extracted by the parameter set extraction unit, from the ion channel value storage unit, using an ion channel characteristics deriving unit. The antiarrhythmic agent effect evaluation method provides the same advantage as the antiarrhythmic agent effect evaluation system.

Advantageous Effects

According to the present invention, since it is possible to simply determine ion channel characteristics of a patient by measuring a cardiac action potential of the patient, there is an advantage of avoiding a risk of gathering cardiomyocyte s of the patient.

In addition, there is an advantage of simulating a treatment effect of an antiarrhythmic agent which has nature of exhibiting a significantly different effect and a different level of safety for each individual, in accordance with an individual's ion channel characteristics, without directly applying the antiarrhythmic agent to a patient.

In addition, advantages of the present invention are not limited to those described above but rather the ordinarily skilled in the art would appreciate that there are also other advantages, from the following description.

Figure 1:
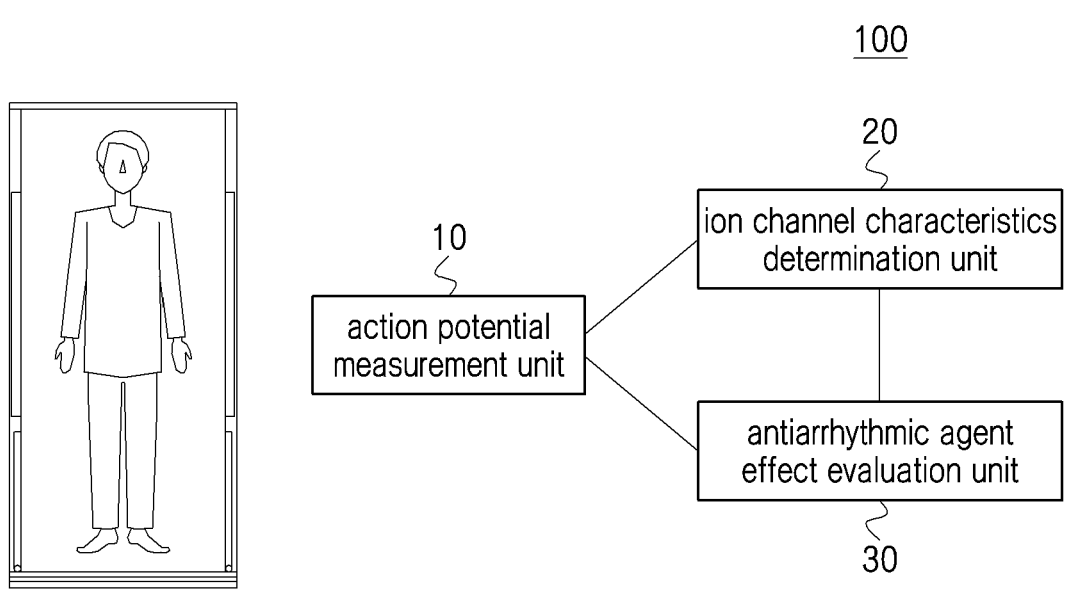
FIG. 1 is a diagram illustrating an overall structure of an antiarrhythmic agent effect evaluation system according to one embodiment of the present invention.

Reference numerals used in the drawings are described below.
  100: antiarrhythmic agent effect evaluation system
  10: action potential measurement unit
  20: ion channel characteristics determination unit
  21: ion channel value storage unit
  22: parameter extraction unit
  23: parameter set setting unit
  24: parameter set selection unit
  25: graph generation unit
  26: parameter set extraction unit
  27: ion channel characteristics deriving unit
  30: antiarrhythmic agent effect evaluation unit

DETAILED DESCRIPTION OF THE INVENTION

Hereinafter, preferred embodiments of the present invention will be described with reference to the accompanying drawings. The preferred embodiments are provided to help the ordinarily skilled in the art to understand the present invention, and are not intended to limit the scope of the present invention. Detailed descriptions of known functions and components incorporated herein will be omitted when it may make the subject matter of the present invention unclear.

Each element and its shape may be schematically or exaggeratedly illustrated to help understanding of the present invention. Some elements provided for a real product may not be illustrated or may be omitted in the drawings or description. The drawings should be construed only to aid understanding of the present invention. Throughout the drawings, the same reference numerals will refer to the same or like parts.

It will be further understood that the terms "comprises" or "includes" and/or "including", when used in this specification, specify the presence of stated features, regions, integers, steps, operations, elements, and/or components, but do not preclude the presence or addition of one or more other features, regions, integers, steps, operations, elements, components, and/or groups thereof.

FIG. 1 is a diagram illustrating an overall structure of an antiarrhythmic agent effect evaluation system 100 according to one embodiment of the present invention.

The antiarrhythmic agent effect evaluation system 100 includes an action potential measurement unit 10, an ion channel characteristics determination unit 20, and an antiarrhythmic agent effect simulative evaluation unit 30.

Figure 2:
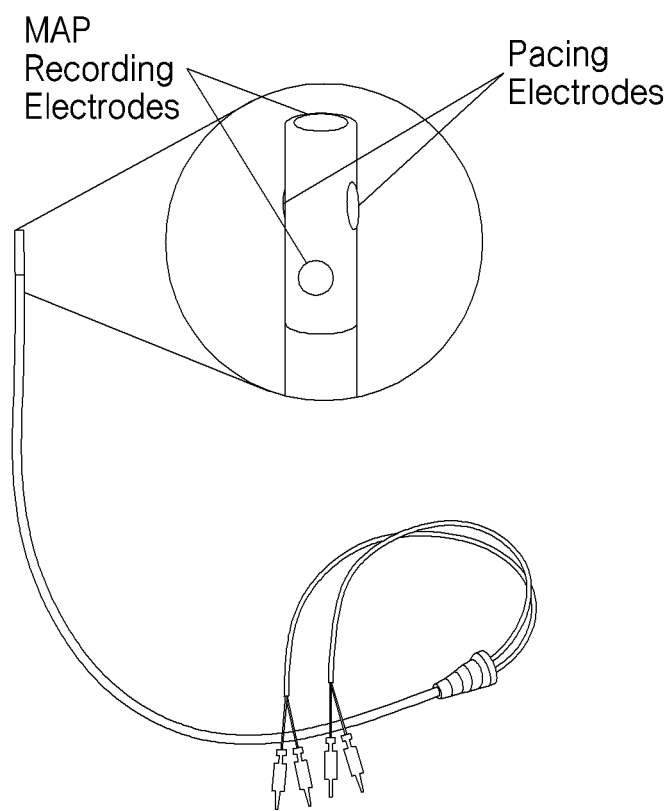
FIG. 2 is a diagram illustrating a Franz catheter.
Figure 3:
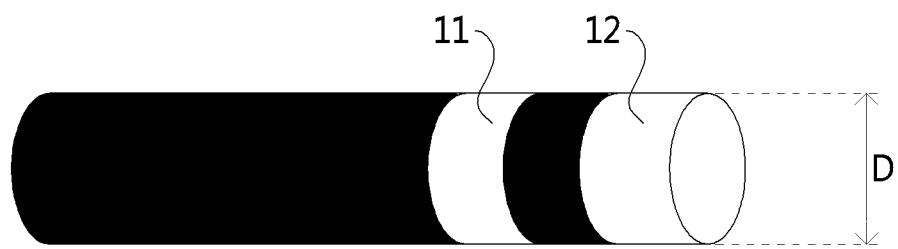
FIG. 3 is a diagram illustrating a catheter disclosed in Korean Patent No. 10-1443156. (Sep. 16, 2014)
Figure 4:
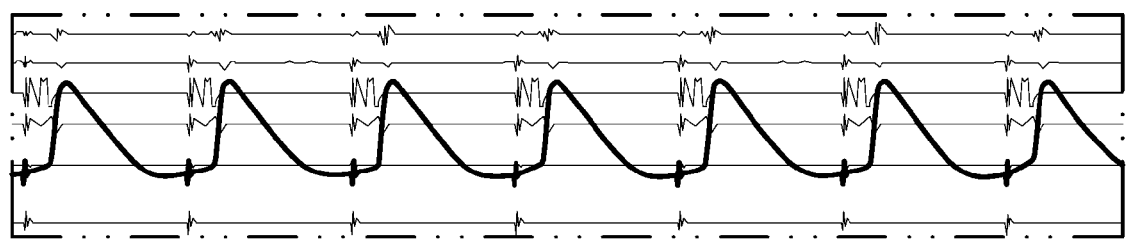
FIG. 4 is a diagram illustrating waveform s of a cardiac action potential of a patient.
Figure 5:
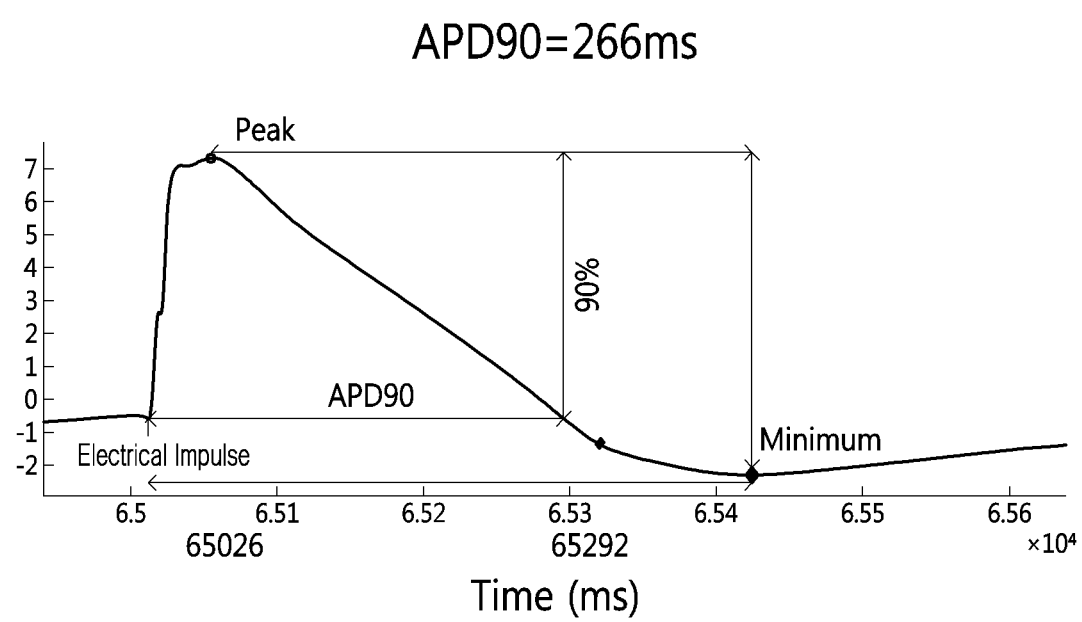
FIG. 5 is a graph illustrating one waveform of the waveforms of the cardiac action potential of FIG. 4.
Figure 6:
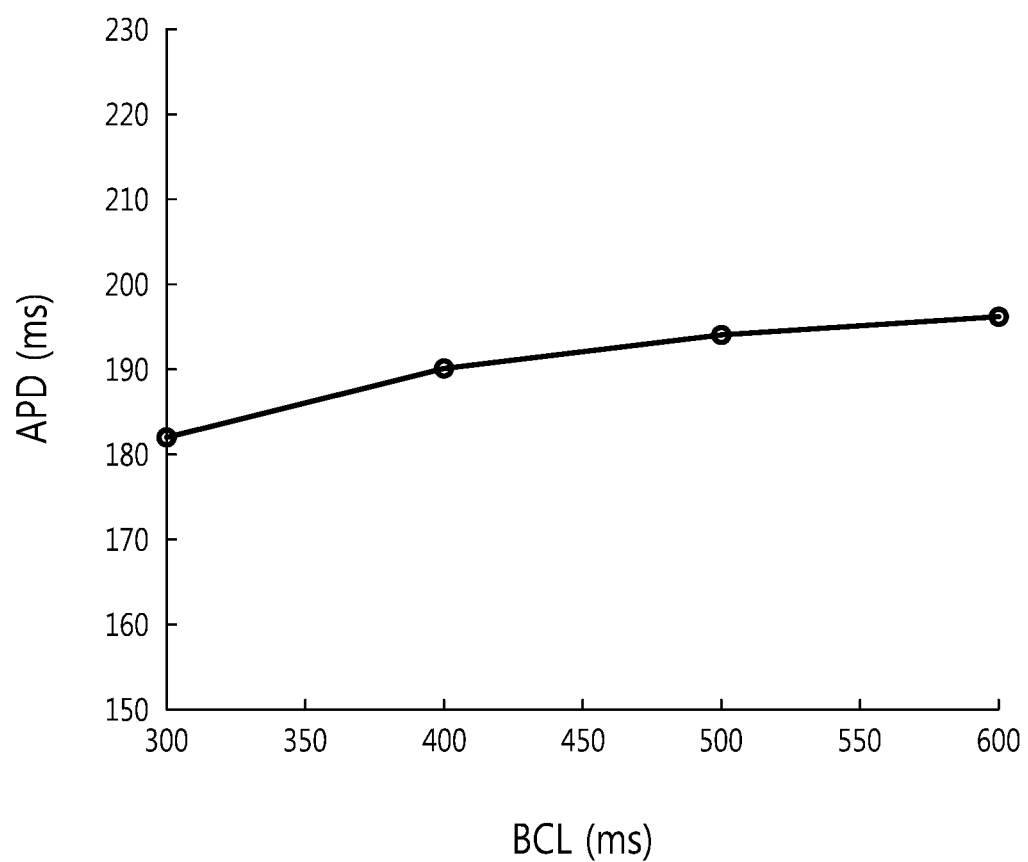
FIG. 6 is a graph illustrating a record of a monophasic action potential (MAP) of a patient, calculated from the waveform of FIG. 5.

Arrhythmia refers to a symptom in which the heart beat is irregular, too fast, or too slow because an electrical impulse does not occur or is not transmitted in a heart, thereby obstructing regular contraction of the heart. For diagnosis of arrhythmia, a cardiac action potential that is an action potential at cardiomyocytes is necessarily measured. Therefore, an action potential measurement unit 10 is required to measure a cardiac action potential of a patient. Specifically, the cardiac action potential is measured using a catheter, and various pacing protocols that can electrically stimulate cardiomyocytes are used to record the cardiac action potential. The catheter may be a typical catheter used for catheter ablation for treatment of arrhythmia, for example, a Franz catheter illustrated in FIG. 2. Alternatively, a dedicated catheter disclosed in Korean Patent No. 1443156 (Sep. 16, 2014) and illustrated in FIG. 3 may be used. The catheter illustrated in FIG. 2 includes a first electrode 11 and a second electrode 12 in which a cross sectional area D of each electrode can be arbitrary adjusted according to a contact state. In the case of the catheter illustrated in FIG. 3, in either case in which the electrodes are in a good contact, an overall good contact, or a poor contact, a cardiac action potential can be measured while adjusting the cross sectional area of the electrodes. Therefore, when the catheter is used in combination with an antiarrhythmic agent effect evaluation system of the present invention, an advantage of the present invention can be maximized. When a cardiac action potential of a patient is measured by the action potential measurement unit 10 and recorded by a pacing protocol, waveforms of a cardiac action potential waveform illustrated in FIG. 4 can be obtained. With reference to the waveforms of FIG. 4, the waveform denoted by "X" is periodically repeated, and is called a cardiac action potential waveform. FIG. 5 is a graph illustrating only one a waveform of the waveforms shown in FIG. 4. A record of a monophasic action potential (MAP) of a patient can be extracted from the graph of FIG. 5. Specifically, a length between a lowest point and a peak in the graph is calculated, and a time that it takes to reach a point corresponding to 90% of the calculated length is measured. Such calculation and measurement are repeated several times, and average values thereof are obtained. Then the average values are plotted and plotting points thereof are connected by a curved line. In this way, a patient's monophasic action potential record of FIG. 6 can be produced.

All antiarrhythmic agent s adjust ion channels of cardiomyocytes. However, there is a problem that effects and stability of the antiarrhythmic agents vary according to states of ion channels of an individual. Therefore, it is necessary to determine characteristics of ion channels for each individual before applying an antiarrhythmic agent to the individual. An ion channel characteristics determination unit 20 is used to determine a patient's ion channel characteristics by using a cardiac action potential measured by the action potential measurement unit 10. The ion channel characteristics determination unit 20 determines ion channel characteristics of a patient using a reverse engineering theory, and details thereof will be described below.

After the ion channel characteristics of a patient are determined by the ion channel characteristics determination unit 20, the antiarrhythmic agent effect simulative evaluation unit 30 can perform simulative evaluation of a treatment effect of an antiarrhythmic agent while reflecting the ion channel characteristics. That is, the antiarrhythmic agent effect simulative evaluation unit 30 is a virtual simulator for simulating a treatment effect, and can virtually evaluate a treatment effect of various antiarrhythmic agents by applying the antiarrhythmic agents to the patient's determined ion channel characteristics. The antiarrhythmic agent effect simulative evaluation unit 30 may be a commercially available program or device.

Figure 7:
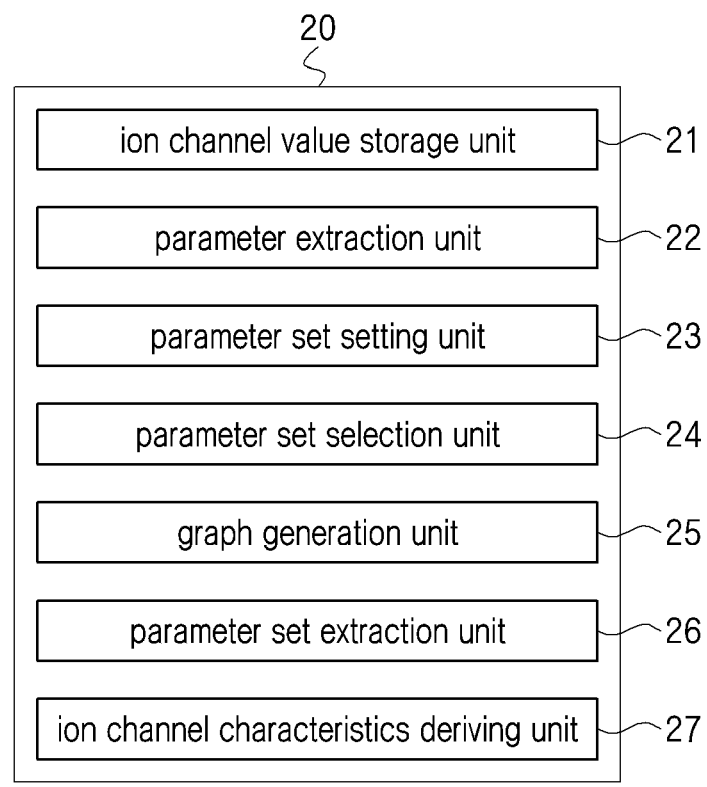
FIG. 7 is a diagram illustrating the structure of an ion channel characteristics determination unit according to one embodiment of the present invention.

As described above, the antiarrhythmic agent effect evaluation system 100 according to one embodiment of the present invention can evaluate a treatment effect in the following manner: first, the action potential measurement unit 10 measures a cardiac action potential of a patient using a catheter and records the cardiac action potential using the pacing protocol; second, the ion channel characteristics determination unit 20 determines ion channel characteristics of the patient, using the cardiac action potential of the patient; and finally, the antiarrhythmic agent effect simulative evaluation unit virtually applies various antiarrhythmic agents to the patient's determined ion channel characteristics and evaluates a treatment effect thereof. Therefore, it is possible to eliminate the risk of gathering a patient's cardiomyocytes to determine the patient's ion channel characteristics, and can simulate evaluation of a treatment effect of various antiarrhythmic agents that exhibit different effects and different levels of safety according to ion channel characteristics for each individual. Hereinafter, technical features of the ion channel characteristics determination unit 20 that determines ion channel characteristics through the reverse engineering theory will be described in detail below FIG. 7 is a block diagram illustrating the structure of the ion channel characteristics determination unit 20 according to one embodiment of the present invention.

The ion channel characteristics determination unit 20 includes an ion channel value storage unit 21, a parameter extraction unit 22, a parameter set setting unit 23, a parameter set selection unit 24, a graph generation unit 25, a parameter set extraction unit 26, and an ion channel characteristics deriving unit 27.

The ion channel value storage unit 21 stores maximum values of physiological conductance (hereinafter, referred to as ion channel maximum values) of all ion channels for each healthy person. For example, maximum values of ion channels, such as INa, ICaL, IK1, IKr, INak, INaca, ITo, and IKur ion channels, are stored. The stored ion channel maximum values can be changed by a user, and can be updated through a wireless or cable communication network.

The parameter extraction unit 22 extracts ion channel maximum values of n ion channels associated with ion channel modeling from the ion channel maximum values stored in the ion channel value storage unit 21, sets the extracted ion channel maximum values respectively as parameters P1 to Pn. Here, since the ion channels associated with ion channel modeling typically include INa, ICaL, IK1, IKr, INak, INaca, ITo, and IKur ion channels, n is preferably 8. Therefore, 8 ion channel maximum values of the INa, ICaL, IK1, IKr, INak, INaca, ITo, and IKur ion channels, stored in the channel value storage unit 21, are set as the parameters P1 to P8, respectively. For example, the maximum value of the INa ion channel is set as the parameter P1, the maximum value of the ICaL ion channel is set as the parameter P2, the maximum value of the IK1 ion channel is set as the parameter P3, the maximum value of the IKr ion channel is set as the parameter P4, the maximum value of the INak ion channel is set as the parameter P5, the maximum value of the INaca ion channel is set as the parameter P6, the maximum value of the ITo ion channel is set as the parameter P7, and the maximum value of the IKur ion channel is set as the parameter P8. However, these settings are only an example and can be freely set by a user. In addition, the parameter extraction unit 22 can arbitrarily change the values of the parameters P1 to Pn by multiplying the maximum values by any adjustment value ranging from 0 to 2 so that the parameters P1 to Pn can have uniformly distributed values. Here, a range of 0 to 2, which is a range of the adjustment value, is exemplary but can be freely set by a user. However, when the parameters are adjusted to be more than two fold, a parameter distribution range is excessively large. Therefore, the adjustment value is set preferably not to be greater than 2. Since the parameters P1 to Pn extracted by the parameter extraction unit 22 are converted to have a uniform distribution, when a certain parameter is extracted, all of the parameters can be selected with an equal probability regardless of the range of the adjustment value, 0 to 2.

The parameter set setting unit 23 selects a set of n parameters K or more times from the parameters P1 to Pn, which are converted to be uniformly distributed by the parameter extraction unit, and sets the K sets of parameters respectively as parameter sets S1 to Sk. Namely, since n is 8 as described above, 8 arbitrary parameters are extracted for each time from among the parameters P1 to P8 that are converted to be within a range of zero to two fold. Through this process, a parameter set S1 (P1 to P8), a parameter set S2 (P1 to P8), ..., and a parameter set Sk (P1 to P8) can be set. In this case, for reliable extraction, K may be preferably equal to 10,000 or greater. When K is 10,000, the number of parameter sets S is 10,000.

Figure 8:
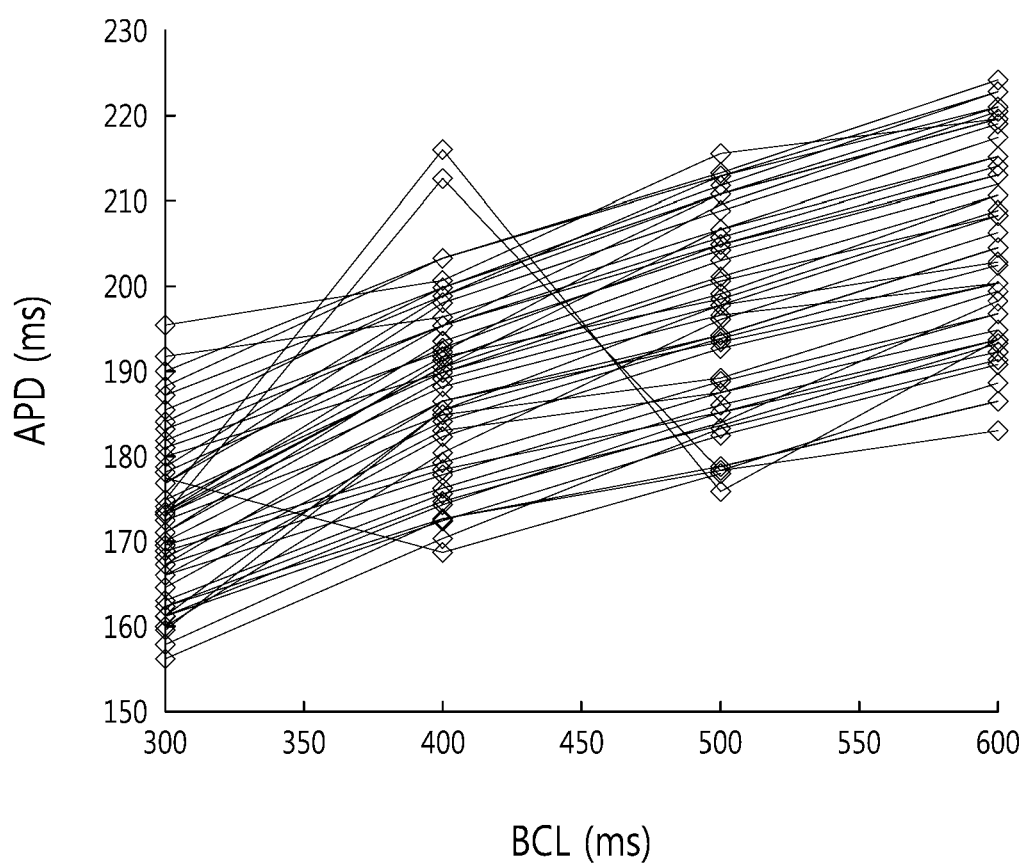
FIG. 8 is a diagram illustrating 10,000 pacing interval relation graphs generated by simulatively executing a pacing protocol 10,000 times.

The parameter set selection unit 24 randomly selects one parameter set Si (i–K) M or more times from the parameter sets Si to Sk, which are set by the parameter set setting unit 23. Here, M is also equal to or greater than 10,000 to improve selection reliability. When M is 10,000, the number of selected parameter sets is 10,000. Next, the pacing protocol simulation is repeatedly performed with respect to the selected M or more parameter sets Si. As briefly described above, the pacing protocol is a sequence of events that electrically stimulate cardiomyocytes. By electrically stimulating the cardiomyocytes, an action potential duration of the cardiomyocyte s can be obtained. Using this data, the graph generation unit 25 can generate a pacing interval relation graph. The parameter set Si is a kind of a parameter and is a parameter including the parameters P1 to Pn. The parameters P1 to Pn respectively represent the ion channel maximum values of n ion channels. Accordingly, it is considered that a pacing protocol is simulatively performed with respect to the cardiomyocytes representing the ion channel maximum value s of the n ion channels. When a pacing protocol is performed each time, one pacing interval relation graph can be generated. Therefore, as in the case of selection of the parameter set Si, it is preferable to perform the pacing protocol 10,000 or more times. Meanwhile, since the parameter set Si is randomly selected, a certain parameter set, any of S1 to Sk, can be repeatedly selected many times or selected only once. In either case, the total number of simulative executions of the pacing protocol performed with respect to all of the selected parameter sets needs to be 10,000 or greater. FIG. 8 illustrates 10,000 pacing interval relation graphs obtained by performing the simulation execution of the pacing protocol 10,000 times. The vertical axis BCL of the graph denotes a cycle length of each ion channel and the horizontal axis APD90 denotes an action potential duration (APD).

Figure 9:
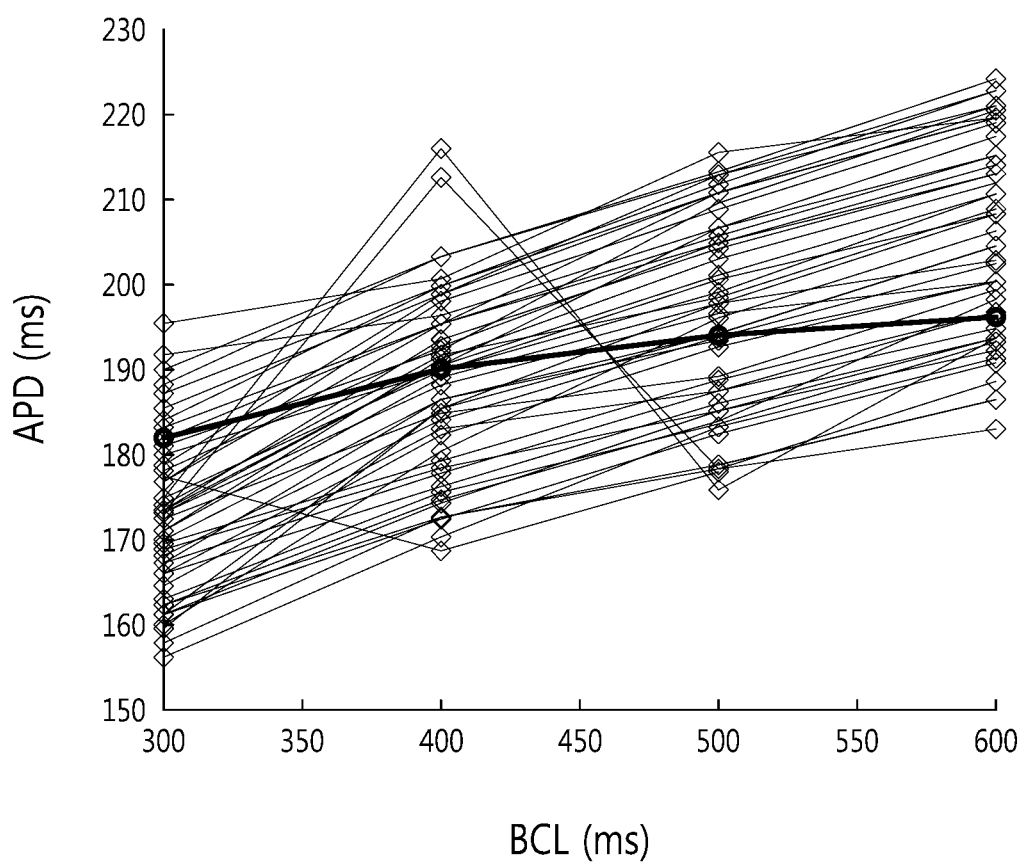
FIG. 9 is a diagram in which a patient's action potential graph is superimposed on the graph of FIG. 8.

The parameter set extraction unit 26 checks the action potential duration on the horizontal axis of the graph generated by the graph generation unit 25, compares the action potential duration and the monophasic action potential of the patient, which is measured and recorded by the action potential measurement unit 10, calculates an error between the action potential duration and the monophasic action potential, and extracts all the parameter sets Sj (j=K) having an error range smaller than a predetermined value. The reason of the error calculation is that the monophasic action potential of a patient cannot be always compared with a pacing interval relation graph similar to the monophasic action potential of the patient when the monophasic action potential of the patient is compared with at least 10,000 graphs illustrated in FIG. 5. That is, it is because when errors are calculated and all the parameters Sj (j=K) having an error smaller than a predetermined value are extracted, it is possible to obtain more reliable results in determining the patient's ion channel characteristics. The error calculation is performed using a variance. Specifically, differences between each of the action potential durations on all the graphs generated by the graph generation unit 25 and a patient's monophasic action potential that is measured and recorded by the action potential measurement unit 10 are individually raised to the second power, the squares of the differences are totaled, and a square root of the sum of the squares is calculated to produce an error. All the parameter sets Sj having an error range smaller than a predetermined value are considered to have ion channel characteristics similar to those of a patient. The error range can be arbitrarily set by a user. Generally, it is set to a value of 95% of the average of the 10,000 pacing interval graphs shown in FIG. 8. With reference to FIG. 9, it is shown that all of the graphs having an error smaller than a predetermined value are significantly similar to the patient's monophasic action potential graph. Thus, extraction of the parameter set Sj is performed to extract parameter sets included in the pacing interval relation graphs having an error range smaller than a predetermined value.

Figure 10:
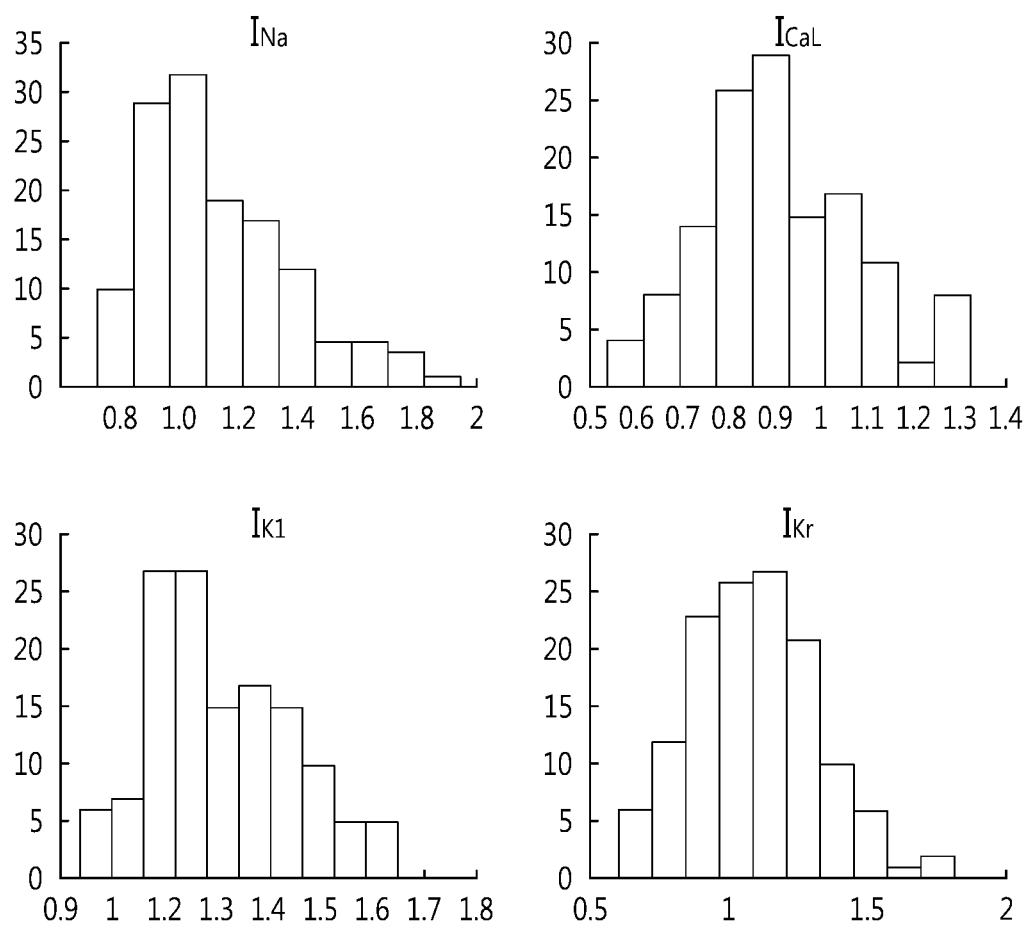
FIG. 10 is a diagram illustrating maximum values of a patient's INa, ICaL, IK1, and IKr ion channels determined on the basis of FIG. 9.

After the parameter set Sj included in the pacing interval relation graph similar to the monophasic action potential graph of a patient is extracted by the parameter set extraction unit 26, the ion channel characteristics deriving unit 27 derives ion channel characteristics of the patient by extracting the ion channel maximum values represented by the n parameters included in the extracted parameter set Sj, from the ion channel value storage unit. The parameters P1 to Pn are included in the parameter set Sj. Since the parameters P1 to Pn are parameters representing the maximum values of the ion channels, it can be concluded that the patient's ion channel characteristics are similar to the parameters P1 to Pn. The maximum values of the patient's INa, ICaL, IK1, and IKr ion channels determined according to FIG. 9 are shown in FIG. 10.

The ion channel characteristics determination unit 20 that is a constituent element of the antiarrhythmic agent effect evaluation system 100 of the present invention can derive the patient's ion channel characteristics by contrasting the patient's action potential graph with the pacing interval relation graphs generated on the basis of the ion channel maximum values of healthy people. Therefore, it can be considered that the reverse engineering theory is used in this process. Although the results are presumption for the patient's ion channel characteristics, it is proved in clinics that the presumption is highly accurate.

The antiarrhythmic agent effect evaluation system 100 can be implemented as an antiarrhythmic agent effect evaluation method having substantially the same features as the antiarrhythmic agent effect evaluation system 100 according to one embodiment of the present invention although the system and the method belong to different categories. This will be described below with reference to FIGS. 11 and 12.

Figure 11:
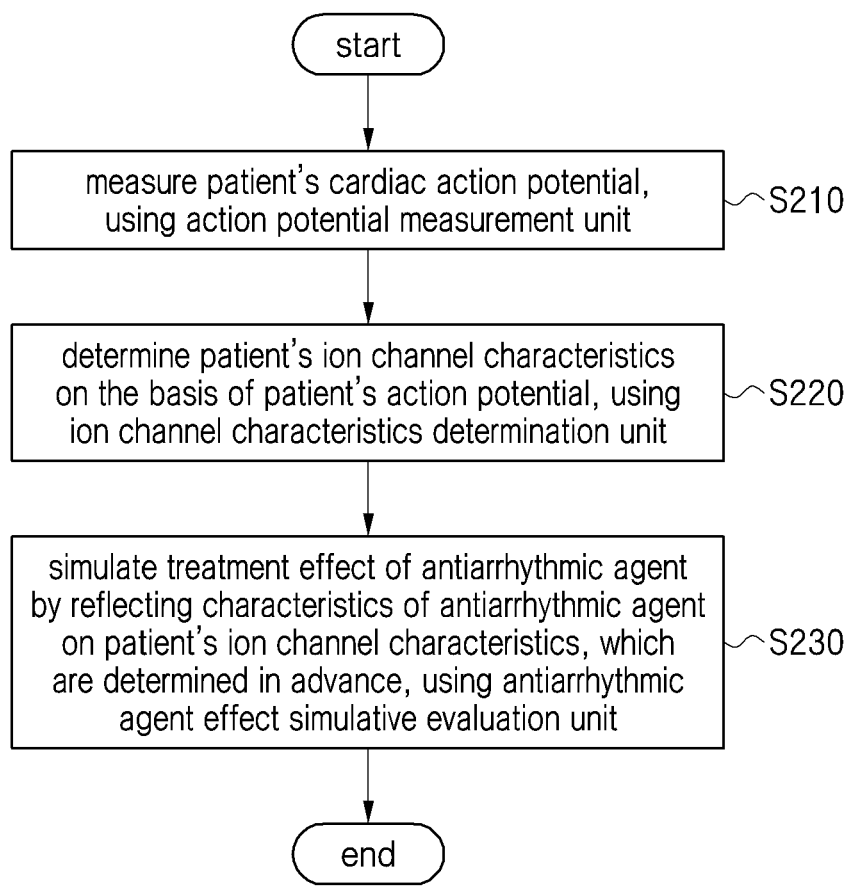
FIG. 11 is a diagram illustrating a flowchart of an antiarrhythmic agent effect evaluation method according to another embodiment of the present invention.

FIG. 11 is a diagram illustrating a flowchart of an antiarrhythmic agent effect evaluation method according to one embodiment of the present invention.

First, an action potential measurement unit 10 measures a cardiac action potential of a patient in Step S210. Next, an ion channel characteristics determination unit 20 determines ion channel characteristics of the patient on the basis of action potential measured by the action potential measurement unit 10 in Step S220. Finally, an antiarrhythmic agent effect simulative evaluation unit 30 simulates a treatment effect of antiarrhythmic agents by reflecting characteristics of the antiarrhythmic agents on the determined ion channel characteristics of the patient in Step S230. An overall sequence is in order of from Step S210 to Step S230. A method of determining a patient's ion channel characteristics based on the reverse engineering theory, which is a key technical feature of the present invention, will be described with reference to FIG. 8.

Figure 12:
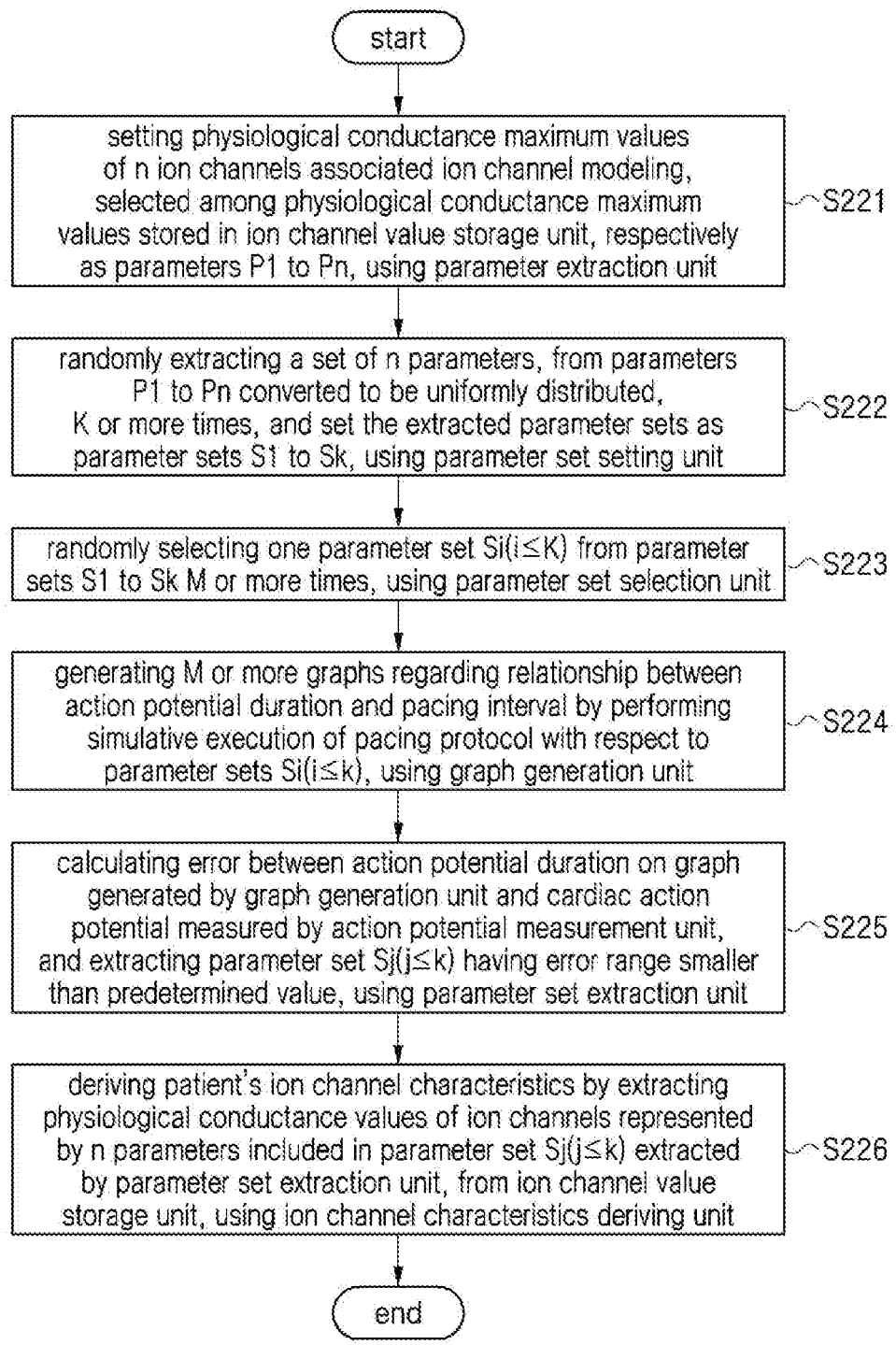
FIG. 12 is a diagram illustrating a flowchart a method of determining ion channel characteristics of a patient, which is performed by an ion channel characteristics determination unit.

FIG. 12 is a diagram illustrating a flowchart of a method of determining ion channel characteristics of a patient using the ion channel characteristics determination unit. An ion channel value storage unit 21 is assumed to store ion channel maximum values of all ion channels of each healthy person.

First, a parameter extraction unit 22 extracts physiological conductance maximum values of n ion channels associated with ion channel modeling from among physiological conductance maximum values stored in the ion channel value storage unit 21, sets the extracted values respectively as parameters P1 to Pn, and converts the parameters to be uniformly distributed, in Step S221. Since the ion channels associated with ion channel modeling are typically INa, ICaL, IK1, IKr, INak, INaca, ITo, and IKur ion channels, n is preferably 8. Therefore, 8 values representing the ion channel maximum values of the INa, ICaL, IK1, IKr, INak, INaca, ITo, and IKur ion channels, which are stored in the ion channel value storage unit 21, are extracted, and set respectively as the parameters P1 to P8. For example, the maximum value of the INa ion channel is set as the parameter P1, the maximum value of the ICaL ion channel is set as the parameter P2, the maximum value of the IK1 ion channel is set as the parameter P3, the maximum value of the IKr ion channel is set as the parameter P4, the maximum value of the INak ion channel is set as the parameter P5, the maximum value of the INaca ion channel is set as the parameter P6, the maximum value of the ITo ion channel is set as the parameter P7, and the maximum value of the IKur ion channel is set as the parameter P8. However, these settings are only an example and can be arbitrarily set by a user. In addition, the parameter extraction unit 22 converts the parameters P1 to Pn by multiplying the original values by an adjustment value that is in a range of from 0 to 2 so that the parameters are uniformly distributed. The range of 0 to 2 is set only as an example but can be freely changed by a user. However, when the adjustment value is greater than 2, a distribution range of the parameters is excessively large. Therefore, preferably the adjustment value may be set not to be greater than 2.

Next, a parameter set setting unit 23 selects arbitrary n parameters P1 to Pn K or more times from the parameters converted to be uniformly distributed, and sets the extracted parameters respectively set as parameter sets S1 to Sk in Step S222. When n is 8 as described above, the parameters P1 to P8 converted to be within a range of zero to two fold are randomly extracted K times. Through this process, parameter sets S1(P1 to P8), S2(P1 to P8), . . . , and Sk(P1 to P8) can be set. To secure reliable extraction, preferably K may be at least 10,000. When K is 10,000, the number of the parameter sets may be 10,000.

After the parameter sets Si to Sk are set, a parameter set selection unit 24 selects an arbitrary parameter set Si (i=K) M or more times from the parameter sets S1 to Sk in Step S223, in which M is preferably at least 10,000 for improvement of selection reliability. Subsequently, a graph generation unit 25 simulatively executes a pacing protocol with respect to the selected parameter sets Si (i=K), thereby generating M or more graphs showing a relationship between an action potential duration and a pacing interval in Step S224. Here, the parameter set Si is a kind of a parameter and includes the parameters P1 to Pn, in which the parameters P1 to Pn are parameters representing ion channel maximum values of n ion channels. Therefore, it can be considered that a pacing protocol is simulatively performed with respect to cardiomyocytes representing the ion channel maximum values of n ion channels. When a pacing protocol is performed once, one pacing interval relation graph can be generated. Therefore, as with the section of parameter sets Si, the simulative pacing protocol is preferably performed 10,000 or more times.

After the graph generation unit 25 generates a pacing interval relation graph, a parameter set extraction unit 26 calculates an error between an action potential duration on the graph generated by the graph generation unit 25 and a patient's monophasic action potential measured by the action potential measurement unit 10, and extracts a parameter set Sj (j=K) having an error range that is smaller than a predetermined value in Step S225. Here, the error calculation is performed using a variance. Specifically, differences between each of the action potential durations on all the graphs generated by the graph generation unit 25 and a patient's monophasic action potential measured by the action potential measurement unit 10 are individually raised to the second power, the squares of the differences are totaled, and a square root of the sum is calculated to produce an error. The parameter set Sj having an error range smaller than a predetermined value is considered that its ion channel characteristics are significantly similar to the patient's ion channel characteristics. The error range can be arbitrarily changed by a user, but may be generally set to a value that is 95% of the average of the 10,000 pacing interval relation graphs shown in FIG. 8. With reference to FIG. 9, it is shown that all of the graphs having an error smaller than a predetermined value are significantly similar to the patient's monophasic action potential. Thus, extraction of the parameter set Sj is performed to extract a parameter set included in the pacing interval relation graphs having an error range smaller than a predetermined value.

Finally, an ion channel characteristics deriving unit 27 extracts the ion channel maximum values of the ion channels represented by the n parameters included in the parameter set Sj (j=K) extracted by the parameter set extraction unit 26, from the ion channel value storage unit, and derives the patient's ion channel characteristics in Step S226. The parameter set Sj includes the parameters P1 to Pn. Since the parameters P1 to Pn are parameters representing the ion channel maximum values, it can be concluded that the patient's ion channel characteristics are similar to the parameters P1 to Pn.

Although features of the antiarrhythmic agent effect evaluation method are not described in detail to avoid redundant explanation, the features of the antiarrhythmic agent effect evaluation system 100 described above can also be applied to the antiarrhythmic agent effect evaluation method. For example, in the antiarrhythmic agent effect evaluation method, K and M may be set to 10,000. The antiarrhythmic agent effect evaluation method can be embodied in the form of a computer program. In this case, the computer program may be recorded on a computer-readable recording medium that can store a computer executable program, or can be distributed by a program provider server.

Although a preferred embodiment of the present invention has been described for illustrative purposes, the present invention is not limited to the preferred embodiment. Those skilled in the art will appreciate that various modifications, additions, and substitutions are possible, without departing from the scope and spirit of the present invention as disclosed in the accompanying drawings.

The invention claimed is:

1. An antiarrhythmic agent effect evaluation system comprising:
    an action potential measurement unit that measures a cardiac action potential of a patient;
    an ion channel characteristics determination unit that determines a characteristic of an ion channel of a patient on the basis of the measured cardiac action potential; and
    an antiarrhythmic agent effect simulative evaluation unit that simulates a treatment effect of an antiarrhythmic agent by reflecting a characteristic of the antiarrhythmic agent on the determined characteristic of the ion channel of the patient,
    wherein the ion channel characteristics determination unit comprises:
    an ion channel value storage unit in which physiological conductance maximum values of all ion channels of healthy people are stored;
    a parameter extraction unit that extracts physiological conductance maximum values of n ion channels associated with ion channel modeling from among the physiological conductance values stored in the ion channel value storage unit, sets the extracted physiological conductance maximum values as parameters (P1 to Pn) respectively, and converts the parameters (P1 to Pn) to have a uniform distribution; and
    a parameter set setting unit that extracts parameters (P1 to Pn) K or more times from among the parameters converted to be uniformly distributed, and sets the extracted parameters as parameter sets (S1 to Sk), respectively.

2. The system according to claim 1,
    wherein the action potential measurement unit measures the cardiac action potential of the patient using a catheter and records the measured cardiac action potential using a pacing protocol.

3. The system according to claim 1,
    wherein the ion channel characteristics determination unit comprises:
    a parameter set selection unit that randomly selects a parameter set Si (i=K) M or more times from among the parameter sets S1 to Sk; and
    a graph generation unit that simulatively performs an pacing protocol with respect to the M or more parameter sets Si that are selected, and generates M or more graphs regarding a relationship between an action potential duration and a pacing interval.

4. The system according to claim 3,
    wherein the ion channel characteristics determination unit comprises a parameter set extraction unit that calculates an error between the action potential duration on the graph generated by the graph generation unit and the cardiac action potential measured by the action potential measurement unit, and extracts a parameter set Sj (j=K) having an error range smaller than a predetermined value.

5. The system according to claim 4,
    wherein the ion channel characteristics determination unit comprises an ion channel characteristics deriving unit that derives a patient's ion channel characteristics by extracting physiological conductance values of ion channels represented by n parameters included in the parameter set Sj extracted by the parameter set extraction unit, from the ion channel value storage unit.

6. The system according to claim 4,
    wherein the parameter set extraction unit calculates an error by calculating differences between action potential durations on the graphs generated by the graph generation unit and the patient's cardiac action potential measured by the action potential measurement unit, raising each difference to the second power to produce respective squares, totaling the squares, and calculating a square root of the sum of the squares.

7. The system according to claim 1,
    wherein the n is 8, and the n ion channels include INa, ICaL, IK1, IKr, INak, INaca, ITo, and IKur ion channels.

8. The system according to claim 1, wherein the K is 10,000.

9. The system according to claim 3, wherein the M is 10,000.

10. A antiarrhythmic agent effect evaluation method comprising:
    (a) measuring a cardiac action potential of a patient, using an action potential measurement unit;
    (b) determining an ion channel characteristic of the patient on the basis of the cardiac action potential, using an ion channel characteristics determination unit; and
    (c) simulating a treatment effect of an antiarrhythmic agent by reflecting a characteristic of the antiarrhythmic agent on the determined ion channel characteristic of the patient, using an antiarrhythmic agent effect simulative evaluation unit,
    wherein the ion channel characteristics determination unit comprises an ion channel value storage unit in which physiological conductance values of all ion channels of healthy people are stored,
    wherein the step (b) comprises:
    (b-1) extracting physiological conductance maximum values of n ion channels associated with ion channel modeling from among the physiological conductance values stored in the ion channel value storage unit, setting the extracted values respectively as parameters (P1 to Pn), and converting the parameters to have a uniform distribution, using a parameter extraction unit; and (b-2) extracting a set of n parameters K or more times from the parameters (P1 to Pn) converted to have a uniform distribution and setting the K or more sets of the parameters respectively as parameter sets (S1 to Sk), using a parameter set setting unit.

11. The method according to claim 10,
wherein the step (b) further comprises:
(b-3) randomly selecting one parameter set (Si (i=K)) M or more times from the parameter sets S1 to Sk, using a parameter set selection unit; and
(b-4) performing simulative execution of a pacing protocol with respect to the selected parameter set (Si (i=K)) and generating M or more graphs regarding a relationship between an action potential duration (APD) and a pacing interval, using a graph generation unit.

12. The method according to claim 11,
wherein the step (b) further comprises: (b-5) calculating an error between an action potential duration on the graph generated by the graph generation unit and the cardiac action potential of the patient measured by the action potential measurement unit, and extracting a parameter set (Sj (j=K)) having an error range smaller than a predetermined value, using a parameter set extraction unit.

13. The method according to claim 12,
wherein the step (b) further comprises: (b-6) deriving ion channel characteristics of the patient by extracting physiological conductance values of ion channels represented by the n parameters included in the parameter set (Sj (j=K)) extracted by the parameter set extraction unit, from the ion channel value storage unit, using an ion channel characteristics deriving unit.

14. The method according to claim 10,
wherein the n is 8, and the n ion channels include INa, ICaL, IK1, IKr, INak, INaca, ITo, IKur ion channels.

15. The method according to claim 13,
wherein the n is 8, and the n ion channels include INa, ICaL, IK1, IKr, INak, INaca, ITo, and IKur ion channels.

16. A non-transitory computer-readable recording medium recorded with a program for implementing the method according to claim 10 in a computer.

17. The system according to claim 5,
wherein the n is 8, and the n ion channels include INa, ICaL, IK1, IKr, INak, INaca, ITo, IKur ion channels.

* * * * *